United States Patent [19]
Doebber et al.

[11] Patent Number: 5,847,008
[45] Date of Patent: Dec. 8, 1998

[54] METHOD OF TREATING DIABETES AND RELATED DISEASE STATES

[75] Inventors: Thomas W. Doebber, Scotch Plains; Joel P. Berger, Hoboken, both of N.J.; Gregory D. Berger, Stonington, Conn.; Mark D. Leibowitz, Millburn, N.J.; David E. Moller, Bedminster, N.J.; John T. Olson, Dayton, N.J.; Arthur A. Patchett, Westfield, N.J.; Richard B. Toupence, Scotch Plains, N.J.

[73] Assignee: Merck & Co., Inc., Rahway, N.J.

Related U.S. Application Data

[60] Provisional application No. 60/011,025, Feb. 2, 1996.

[21] Appl. No.: 797,649
[22] Filed: Jan. 31, 1997
[51] Int. Cl.$^6$ .......................... A61K 31/105; A61K 31/10
[52] U.S. Cl. .......................... 514/708; 514/706; 514/866; 514/909; 514/910
[58] Field of Search .................................. 514/706, 708, 514/866, 909, 910

[56] References Cited

U.S. PATENT DOCUMENTS

| | | | |
|---|---|---|---|
| 4,820,867 | 4/1989 | Belanger et al. | 562/478 |
| 5,002,953 | 3/1991 | Hindley | 514/275 |
| 5,232,925 | 8/1993 | Hindley | 514/272 |
| 5,453,443 | 9/1995 | Perrier et al. | 514/570 |
| 5,480,910 | 1/1996 | Holloway et al. | 514/567 |

FOREIGN PATENT DOCUMENTS

| | | |
|---|---|---|
| 0 039 913 | 11/1981 | European Pat. Off. . |
| 0 061 800 | 10/1982 | European Pat. Off. . |
| 0 123 541 | 10/1984 | European Pat. Off. . |
| 0 611 003 A1 | 8/1994 | European Pat. Off. . |
| 0 617 001 A1 | 9/1994 | European Pat. Off. . |
| 0 579 412 A1 | 11/1994 | European Pat. Off. . |
| 2 058 758 | 5/1979 | United Kingdom . |
| WO 93/21166 | 10/1993 | WIPO . |
| WO 94/01420 | 1/1994 | WIPO . |
| WO 94/12461 | 6/1994 | WIPO . |
| WO 94/29285 | 12/1994 | WIPO . |
| WO 95/03288 | 2/1995 | WIPO . |
| WO 95/17183 | 6/1995 | WIPO . |

OTHER PUBLICATIONS

Merck Manual, 16th Ed.: pp. 1039–1040 (1992).
Gordon, et al., *Am. J. Med.*, 62: pp 707–714 (1977).
Stamfer, et a., *New England J. Med.*: 325, pp. 373–381 (1991).
Kannel, et al., *Ann. Internal Med.*, 90: pp. 85–91 (1979).
Elbrecht, et al., *BBRC*, 224: pp. 431–437 (1996).
A. Schmidt et al., *Molecular Endocrinology*, 6: pp. 1634–1641 (1992).
National Cholesterol Educ. Prog., *JAMA*, 269: pp. 3015–3023 (1993).
T. Sher et al., *Biochem*,. 32: pp. 5598–5604 (1993).
R.J. Havel et al., *Metabolic Basis of Inherited Disease*, 6th Ed.: pp. 1129–1138, (1989).

*Primary Examiner*—Theodore J. Criares
*Attorney, Agent, or Firm*—Richard C. Billups; David L. Rose

[57] ABSTRACT

The instant invention is concerned with acetylphenols which are useful as antiobesity and antidiabetic compounds. Compositions and methods for the use of the compounds in the treatment of diabetes and obesity and for lowering or modulating triglyceride levels and cholesterol levels or raising high density lipoprotein levels or for increasing gut motility or for treating atherosclerosis are also disclosed.

23 Claims, No Drawings

METHOD OF TREATING DIABETES AND RELATED DISEASE STATES

This application is a continuation-in part and claims priority to U.S provisional application: application Ser. No. 60/011025 filed Feb. 2, 1996 which is herein incorporated by reference in its entirety.

This application is related to the following U.S. non-provisional applications: Ser. No. 08/797,650 filed Jan. 31, 1997 which is herein incorporated by reference in its entirety.

BACKGROUND OF THE INVENTION

Diabetes refers to a disease process derived from multiple causative factors and characterized by elevated levels of plasma glucose or hyperglycemia. Uncontrolled hyperglycemia is associated with increased and premature mortality due to an increased risk for microvascular and macrovascular diseases, including nephropathy, neuropathy, retinopathy, hypertension, stroke, and heart disease. Therefore, control of glucose homeostasis is a critically important approach for the treatment of diabetes.

Type I diabetes (IDDM) is the result of an absolute deficiency of insulin, the hormone which regulates glucose utilization. Type II, noninsulin dependent diabetes mellitus (NIDDM) is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver.

The several treatments for NIDDM, which has not changed substantially in many years, are all with limitations. While physical exercise and reductions in dietary intake of calories will dramatically improve the diabetic condition, compliance with this treatment is very poor because of well-entrenched sedentary lifestyles and excess food consumption, especially high fat-containing food. Increasing the plasma level of insulin by administration of sulfonylureas (e.g. tolbutamide, glipizide) which stimulate the pancreatic β-cells to secrete more insulin or by injection of insulin after the response to sulfonylureas fails, will result in high enough insulin concentrations to stimulate the very insulin-resistant tissues. However, dangerously low levels of plasma glucose can result from these last two treatments and increasing insulin resistance due to the even higher plasma insulin levels could theoretically occur. The biguanides increase insulin sensitivity resulting in some correction of hyperglycemia. However, the two biguanides, phenformin and metformin, can induce lactic acidosis and nausea/diarrhea, respectively.

Thiazolidinediones (glitazones) are a recently disclosed class of compounds that are suggested to ameliorate many symptoms of NIDDM. These agents increase insulin sensitivity in muscle, liver and adipose tissue in several animal models of NIDDM resulting in complete correction of the elevated plasma levels of glucose, triglycerides and nonesterified free fatty acids without any occurrence of hypoglycemia. However, serious undesirable effects have occurred in animal and/or human studies including cardiac hypertrophy, hemadilution and liver toxicity resulting in few glitazones progressing to advanced human trials.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. See the *Merck Manual,* 16th Ed. 1992 (see for example pp. 1039–1040) and "Structure and Metabolism of Plasma Lipoproteins" in *Metabolic Basis of Inherited Disease,* 6th Ed. 1989, pp. 1129–1138. One form of hyperlipidemia is hypercholesterolemia, characterized by the existence of elevated LDL cholesterol levels. The initial treatment for hypercholesterolemia is often to modify the diet to one low in fat and cholesterol, coupled with appropriate physical exercise, followed by drug therapy when LDL-lowering goals are not met by diet and exercise alone. LDL is commonly known as the "bad" cholesterol, while HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, but the quantities needed to achieve HDL raising are associated with undesirable effects, such as flushing.

It is suggested that thiazolidinedione compounds exert their effects by binding to the peroxisome proliferator activated receptor (PPAR) family of receptors, controlling certain transcription elements having to do with the biological entities listed above. See Hulin et al., Current Pharm. Design (1996) 2, 85–102. Three sub-types of PPARs have been discovered and described; they are PPARα, PPARγ and PPARδ. PPARα is activated by a number of medium and long-chain fatty acids, and it is involved in stimulating β-oxidation of fatty acids. PPARAα is also involved with the activity of fibrates in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in LDL cholesterol, and they are used particularly for the treatment of hypertriglyceridemia.

The PPARγ receptor subtypes are involved in activating the program of adipocyte differentiation and are not involved in stimulating peroxisome proliferation in the liver. The DNA sequences for the PPARγ receptors are described in Elbrecht, et al., BBRC 224;431–437 (1996). Although peroxisome proliferators, including the fibrates and fatty acids, activate the transcriptional activity of PPAR's, only prostaglandin $J_2$ derivatives have been identified as natural ligands of the PPARγ subtype, which also binds thiazolidinedione antidiabetic agents with high affinity. The glitazones have been shown to bind exclusively to the PPARγ subtype.

The human nuclear receptor gene PPARδ (hPPARδ) has been cloned from a human osteosarcoma cell cDNA library and is fully described in A. Schmidt et al., *Molecular Endocrinology,* 6 :1634–1641 (1992), herein incorporated by reference. It should be noted that PPARδ is also referred to in the literature as PPARβ and as NUC1, and each of these names refers to the same receptor; in Schmidt et al, the receptor is referred to as NUC1.

SUMMARY OF THE INVENTION

This invention is concerned with the compounds of formula I below and its analogs, pharmaceutically acceptable salts thereof, and bioprecursors thereof, which differ from the thiazolidinediones in that they lack the thiazolidinedione moiety and they do not lead to the array of toxicity's associated with the thiazolidinediones. The instant compounds are effective in treating diabetes, atherosclerosis, hyperglycemia, hyperlipidemia and/or obesity because they lower one or more of the following biological entities in manunals; glucose, insulin, triglycerides, fatty acids, cholesterol and the like. Thus, it is an object of this invention to describe such compounds. It is a further object to describe the specific preferred stereoisomers of the substituted compounds. A still further object is to describe processes for the preparation of such compounds. Another object is to describe methods and compositions which use the compounds as the active ingredient thereof. Further objects will become apparent from reading the following description.

DETAILED DESCRIPTION OF THE INVENTION

This invention is a method of using a compound of formula XI or XII:

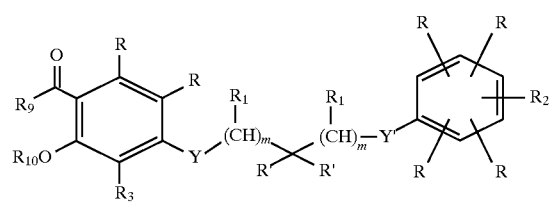

and

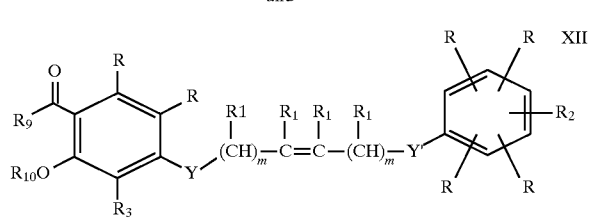

or a pharmaceutically acceptable salt or acid addition salt thereof, or a pharmaceutically acceptable ester thereof, wherein:

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen; amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

Y' is sulfur, sulfoxide, sulfone;

$R_{11}$ is H, alkyl of 1–4 carbon atoms which may be straight chain or branched; alkanoyl of 1–4 carbon atoms which may be straight chain or branched; phenylsulfonyl; tosyl; $NR_{12}$ wherein $R_{12}$ is H, alkyl of 1–4 carbon atoms which may be straight chain or branched; or

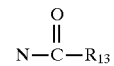

wherein $R_{13}$ is alkyl of 1–4 carbon atoms which may be straight chain or branched, alkoxy of 1–4 carbon atoms which may be straight chain or branched; N—CN, $CH_2$, or C=O;

Y is Y' and oxygen;

each $R_1$ is independently hydrogen or alkyl of 1–3 carbon atoms;

each m is independently an integer from 0–6;

$R_2$ is

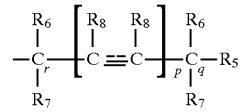

each $R_6$ is independently H or alkyl of 1–4 carbons;
each $R_7$ is independently H, OH, or alkyl of 1–4 carbons;
each $R_8$ is independently H, or alkyl of 1–4 carbons, and is absent when a triple bond is present;

$R_5$ is $COOR_4$; $CH_2OH$; CHO; tetrazole; $NHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is

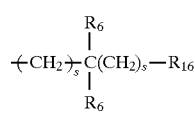

wherein each s is independently 0–3;

$R_{16}$ is

A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

R14 is OH, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl, acyl of 1 to 6 carbon atoms or perfluoroalkyl of 1 to 4 carbon atoms;

r and q are each independently 0–20 provided that the total of r and q does not exceed 20;

p is 0 or 1;

$R_3$ is alkyl of 1 to 6 carbon atoms which may be straight chain or branched; or alkenyl of 3 to 6 carbon atoms which may be straight chain or branched as illustrated in formulas IV and V;

$R_9$ is alkyl of 1 to 6 carbon atoms which may be straight chain or branched; alkoxy of 1 to 6 carbon atoms which may be straight chain or branched; or $(CH_2)_r R_5$; and $R_{10}$ is H; alkyl of 1 to 6 carbon atoms which may be straight chain or branched;

or $R_4OCH_2—$.

In one embodiment of the invention the compounds of formula XI and XII also include the following:
$R_2$ is

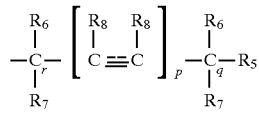

all other definitions remaining the same, except that when one of the $R_7$ groups is hydroxy, Y' may be oxygen.

As used herein, the terms "each independently" or the equivalents thereof are employed to described a number of possible position isomers and/or structural variations.

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

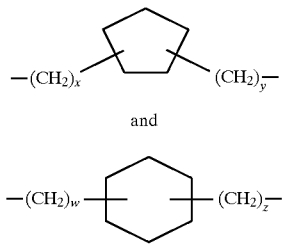

wherein: x and y=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon—carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term alkoxy represents an alkyl group of indicated carbon atoms attached through an oxygen linkage.

The term halo as used herein, represents fluoro, chloro, bromo or iodo.

The compounds of the present invention may be prepared by several different routes which are well published in the art. See EP 106565 B, incorporated by reference herein in its entirety.

According to one method a compound of formula I is reacted with an optionally alkyl substituted alkenyl halide of formula II wherein X is halogen and each $R_6$ is independently H or alkyl of 1–4 carbon atoms to yield the corresponding 2-hydroxy-4-alkenyloxy-acetophenone of formula III. The compound of formula III is then subjected to a Claisen rearrangement to yield a 2,4-dihydroxy-3-alkenyl-acetophenone compound of formula IV. This rearrangement occurs on heating the compound of formula III either neat or in a high boiling solvent, such as a halogenated hydrocarbon, e.g., dichlorobenzene, at from about 160° to about 210° C. The double bond in the compound of formula IV may then be reduced, e.g., by catalytic hydrogenation such as Pd/C, to yield the corresponding saturated compound of formula V.

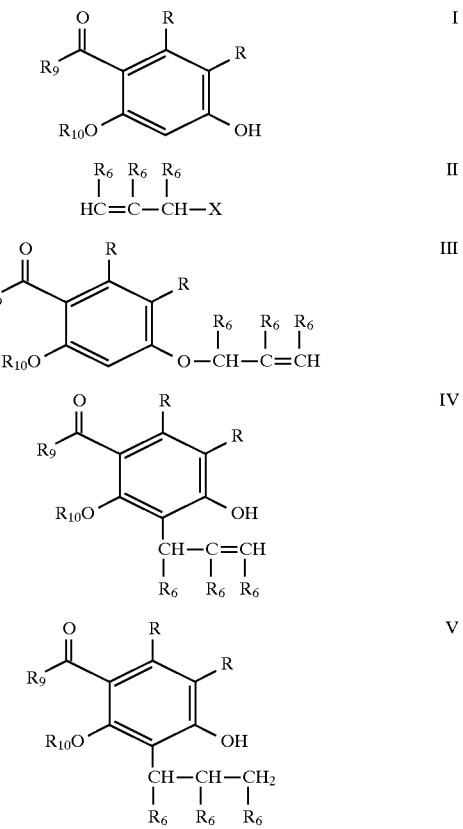

The compound of formula V is then reacted with a dihaloalkane of formula VIa or a dihaloalkene of formula VIb wherein X, R and m have the meaning given previously, to yield a 4-(haloalkyloxy)-3-alkyl-2-hydroxyacetophenone compound of formula VII. The reaction takes place by refluxing a mixture of the compounds of formulas V and VIa or VIb in an inert solvent such as, for example, methylethylketone (MEK), acetone, tetrahydrofuran (THF), triglyme or dichloromethane in the presence of a base. The reflux temperature is preferably in the range of from about 60° to about 130° C. The base may be an alkali metal carbonate, for example, $Li_2CO_3$, $Na_2CO_3$ or $K_2CO_3$.

Specific examples of dihaloalkane compounds of formula VIa are 1,3-dibromopropane, 2-methyl-1,3-dibromopropane, 2,2-dimethyl-1,3-dibromopropane, 3-chloro-2-chloromethyl-1-propene, 1,3-dibromobutane, 1,4-dibromobutane, 1,5-dibromopentane, 1,6-dibromohexane, 1,7-dibromoheptane, 1,8-dibromooctane, 1,9-dibromononane, 1,10-dibromodecane, and 1,12-dibromododecane. A specific example of a dihaloalkene compound of formula VIb is 1,4-dibromo-2-butene.

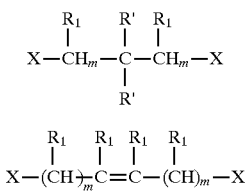

A compound of formula II is then react with a compound of formula V to yield a 4-alkenyloxy-3-alkyl-2-hydroxy-aceto-phenone compound of formula IX which is then epoxidized with an organic peracid such as, for example, m-chloroperbenzoic acid to give the compound of formula VIII.

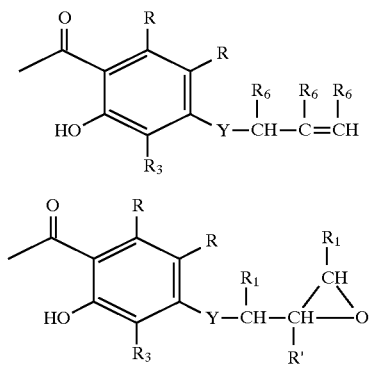

The reaction of a compound of formula VIII with a compound of formula X under the same conditions used to react a compound of formula V with a compound of formula VIa or VIb gives a compound of formula XI or XII.

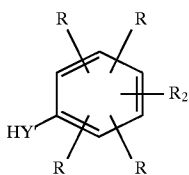

Additional compounds and the method for preparing them included within the scope of this invention are disclosed in U.S. Pat. Nos. 5,453,443, 4,820,867 and EP 0123541 and EP 0617001, all of which are incorporated by reference herein in their entirety.

A preferred compound of the instant method is 4-(3-(4-Acetyl-3-hydroxy-2-propylphenoxy)propylthio)-2,3-dichlorobenzeneacetic acid and its methyl ester;
4-(3-(4-Acetyl-3-hydroxy-2-propylphenoxy)-2-hydroxy-propylthio)-2,3-dichlorobenzeneacetic acid and its methyl ester;
4-(3-(4-Acetyl-3-hydroxy-2-propylphenoxy)propylthio)-2,3-dichlorobenzeneacetic acid-S-oxide and its methyl ester;
4-(3-(4-Acetyl-3-hydroxy-2-propylphenoxy)propylsulfonyl)-2,3-dichlorobenzeneacetic acid and its methyl ester;
4-(3-(4-Acetyl-3-hydroxy-2-propylphenoxy)-2-hydroxypropylthio)-2,3-dichlorobenzeneacetic acid-S-oxide and its methyl ester;
4-(3-(4-Acetyl-3-hydroxy-2-propylphenoxy)-2-hydroxypropylthio)-2,3-dichlorobenzeneacetic acid-S-oxide and its methyl ester;
4-(3-(4-Acetyl-3-hydroxy-2-propylphenoxy)-2-hydroxypropylsulfonyl)-2,3-dichlorobenzeneacetic acid and its methyl ester;
4-(3-(4-Acetyl-3-hydroxy-2-propylphenoxy)propylthio-2-fluorobenzeneacetic acid and its methyl ester;
Sodium Salt of 4-(3-(4-Acetyl-3-hydroxy-2-propylphenoxy)-2-hydroxypropylthio-2-fluorobenzeneacetic acid, monohydrate and its methyl ester;
4-(3-(4-Acetyl-3-hydroxy-2-propylphenoxy)-2-hydroxypropylthio)-2-fluorobenzeneacetic acid-S-oxide and its methyl ester;
4-(3-(4-Acetyl-3-hydroxy-2-propylphenoxy)-2-hydroxypropylsulfonyl)-2-fluorobenzeneacetic acid; and
4-(3-(4-Acetyl-3-hydroxy-2-propylphenoxy)-1-propenylsulfonyl)-2-fluorobenzeneacetic acid and its methyl ester;
4-(3-(4-Acetyl-3-hydroxy-2-propylphenoxy)propylthio-3-fluorobenzeneacetic acid and its methyl ester;
4-(3-(4-Acetyl-3-hydroxy-2-propylphenoxy)-2-hydroxypropylthio)-3-fluorobenzeneacetic acid and its methyl ester;
4-(3-(4-Acetyl-3-hydroxy-2-propylphenoxy)-propylthio-3-chlorobenzeneacetic acid and its methyl ester; 4-(3-(4-Acetyl-3-hydroxy-2-propylphenoxy)-propylthio)-3-chlorobenzeneacetic acid-S-oxide and its methyl ester;
4-(3-(4-Acetyl-3-hydroxy-2-propylphenoxy)-propylsulfonyl)-3-chlorobenzeneacetic acid and its methyl ester;
4-(3-(4-Acetyl-3-hydroxy-2-propylphenoxy)-2-hydroxypropylthio)-3-chlorobenzeneacetic acid and its methyl ester;
4-(3-(4-Acetyl-3-hydroxy-2-propylphenoxy)-2-hydroxypropylthio)-3-chlorobenzeneacetic acid-S-oxide and its methyl ester;
4-(3-(4-Acetyl-3-hydroxy-2-propylphenoxy)-2-hydroxypropylsulfonyl)-3-chlorobenzeneacetic acid and its methyl ester;
4-(3-(4-Acetyl-3-hydroxy-2-propylphenoxy)-propyl-thio)benzeneacetic acid and its methyl ester;
4-(3-(4-Acetyl-3-hydroxy-2-propylphenoxy)-propylsulfonyl)-benzeneacetic acid and its methyl ester;
4-(3-(4-Acetyl-3-hydroxy-2-propylphenoxy)-2-methylpropylthio)-benzeneacetic acid and its methyl ester;
4-(3-(4-Acetyl-3-hydroxy-2-propylphenoxy)-2-hydroxypropylthio)-benzeneacetic acid and its methyl ester;
4-(3-(4-Acetyl-3-hydroxy-2-propylphenoxy)-2-hydroxypropylthio)-3-fluorobenzoic acid and its methyl ester;
4-(3-(4-Acetyl-3-hydroxy-2-propylphenoxy)-2-hydroxypropylthio)-3-fluorobenzoic acid and its methyl ester;
4-(3-(4-Acetyl-3-hydroxy-2-propylphenoxy)-2-hydroxypropylsulfonyl)-3-fluorobenzoic acid and its methyl ester;
4-(3-(4-Acetyl-3-hydroxy-2-propylphenoxy)-propylthio)-3-fluorobenzoic acid-S-oxide, methyl ester and its methyl ester;
4-(3-(4-Acetyl-3-hydroxy-2-propylphenoxy)-propylsulfonyl)-3-fluorobenzoic acid and its methyl ester; and
4-(3-(4-Acetyl-3-hydroxy-2-propylphenoxy)-propylcyanamido)-benzeneacetic acid and its methyl ester.

Compounds of the general Formula XI or XII may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties. They are useful in treating or preventing diabetes, treating obesity, lowering triglyceride levels and prevention of vascular restenosis. They are useful in treating other disorders where insulin resistance is a component including ovarian hyperandrogenism (polycyctic ovarian syndrome). They are also useful in raising high density lipoprotein levels, preventing, halting or slowing the progression of atherosclerotic cardiovascular diseases and related conditions and disease events.

The present invention also provides a compound of the general Formula I or a pharmaceutically acceptable salt thereof for use as an active therapeutic substance.

The present invention further provides a compound of the general Formula I, or a pharmaceutically acceptable ester thereof; or pharmaceutically acceptable salt thereof, for use in the treatment of hyperglycemia (diabetes) in human or non-human animals.

The present invention further provides a compound of the general Formula I, or a pharmaceutically acceptable ester thereof; or pharmaceutically acceptable salt thereof, in combination with known sulfonylureas, other insulin secretogogues as well as insulin for use in the treatment of diabetes treating obesity, lowering triglyceride levels, prevention of vascular restenosis, treating other disorders where insulin resistance is a component including ovarian hyperandrogenism (polycyctic ovarian syndrome), raising high density lipoprotein levels, and preventing, halting or slowing the progression of atherosclerotic cardiovascular diseases and related conditions and disease events.and hypertension in human or non-human animals.

In one aspect, the present invention provides a compound of the general Formula I for use in the treatment of obesity in human or non-human animals. Said compound can be effectively used in combination with other known or proposed strategies for the treatment of obesity or obesity-related disorders; for example, fenfluramine, dexfenfluramine, phentiramine and β3 adrenergic receptor agonist agents.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies. The instant compounds can be effectively used in combination with known therapies for diabetes including insulin, sulfonylureas, biguanides (such as metformin), α-glucosidase inhibitors (such as acarbose) and others.

Two major forms of diabetes mellitus are now recognized. Type I diabetes, or insulin-dependent diabetes, is the result of an absolute deficiency of insulin, the hormone which regulates glucose utilization. Type II diabetes, or non-insulin-independent diabetes, often occurs in the face of normal, or even elevated levels of insulin and appears to be the result of the inability of tissues to respond appropriately to insulin. Most of the Type II diabetics are also obese. Accordingly, in another aspect the present invention provides a method of lowering triglyceride levels which comprises administering, to an animal in need thereof, a therapeutically effective amount of a compound of the formula I or pharmaceutically acceptable salt or ester thereof.

In addition the compounds of the present invention lower or modulate triglyceride levels and/or cholesterol levels and raise HDL plasma levels and are therefore of use in combating medical conditions wherein such lowering (and raising) is thought to be beneficial. Thus they may be used in the treatment of hypertension, obesity, atherosclerotic disease events, diabetes and related conditions by administering to an animal in need thereof, a therapeutically effective amount of a compound of the formula (I) or pharmaceutically acceptable salt thereof. The compositions are formulated and administered in the same general manner as detailed below. They may also contain other active ingredients known for use in the treatment of atherosclerotic disease events, diabetes, hypertension, obesity and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA:cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

In particular the invention provides methods for preventing or reducing the risk of developing atherosclerosis, comprising the administration of a prophylactically effective amount of a compound of formula I alone or in combination with one or more additional pharmaceutically active agents, to a mammal, particularly human, who is at risk of developing atherosclerosis.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The instant invention further provides methods for preventing or reducing the risk of a first or subsequent (where the potential exists for recurrence) atherosclerotic disease event, comprising the administration of a prophylactically effective amount, or more particularly an effective amount of a cholesterol biosynthesis inhibitor, of a compound of formula I alone or in combination with one or more additional pharmaceutically active agents, to a mammal, particularly human, who is at risk for having an atherosclerotic disease event. The term "atherosclerotic disease event" as used herein is intended to encompass coronary heart disease events, cerebrovascular events, and intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. It is intended that persons who have previously experienced one or more non-fatal atherosclerotic disease event are those for whom the potential for recurrence of such an event exists.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein cholesterol, high levels of low density lipoprotein cholesterol, and a family history of atherosclerotic cardiovascular disease. Published guidelines for determining those who are at risk of developing atherosclerotic disease can be found in: National Cholesterol Education Program, Second report of the Expert Panel on Detection, Evaluation, and Treatment of High Blood Cholesterol in Adults (Adult Treatment Panel II), National Institute of Health, National Heart Lung and Blood Institute, NIH Publication No. 93–3095, September 1993; abbreviated version: Expert Panel on Detection, Evaluation, and Treatment of High Blood Cholesterol in Adults, Summary of the second report of the national cholesterol education program (NCEP) Expert Panel on Detection, Evaluation, and Treatment of High Blood Cholesterol in Adults (Adult Treatment Panel II), *JAMA,* 1993, 269, pp. 3015–23. People identified as having one or more of the above-noted risk factors, as well as people who already have atherosclerosis, are intended to be included within the group of people considered to be at risk for having an atherosclerotic disease event.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating or preventing diabetes mellitus and/or hyperglycemia or hypertriglyceridemia, or obesity, or when treating, preventing or slowing the progression of atherosclerosis generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

The compositions are formulated and administered in the same general manner as detailed below. The compounds of the instant invention may be used effectively alone or in combination with one or more additional active agents depending on the desired target therapy. Combination therapy includes administration of a single pharmaceutical dosage formulation which contains a compound of formula I and one or more additional active agents, as well as administration of a compound of formula I and each active agent in its own separate pharmaceutical dosage formulation. For example, a compound of formula I and an HMG-CoA reductase inhibitor can be administered to the patient together in a single oral dosage composition such as a tablet or capsule, or each agent administered in separate oral dosage formulations. Where separate dosage formulations are used, a compound of formual I and one or more additional active agents can be administered at essentially the same time, i.e., concurrently, or at separately staggered times, i.e, sequentially; combination therapy is understood to include all these regimens.

An example of combination treatment or prevention of atherosclerosis may be wherein a compound of formula I is administered in combination with one or more of the following active agents: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor such as melinamide; probucol; nicotinic acid and the salts thereof and niacinamide; a cholesterol absorption inhibitor such as beta-sitosterol; a bile acid sequestrant anion exchange resin such as cholestyramine, colestipol or dialkylaminoalkyl derivatives of a cross-linked dextran; an LDL (low density lipoprotein) receptor inducer; fibrates such as clofibrate, bezafibrate, fenofibrate, and gemfibrizol; vitamin $B_6$ (also known as pyridoxine) and the pharmaceutically acceptable salts thereof such as the HCl salt; vitamin $B_{12}$ (also known as cyanocobalamin); anti-oxidant vitamins such as vitamin C and E and beta carotene; a beta-blocker; an angiotensin II antagonist; an angiotensin converting enzyme inhibitor; and a platelet aggregation inhibitor such as fibrinogen receptor antagonists (i.e., glycoprotein IIb/IIIa fibrinogen receptor antagonists) and aspirin. As noted above, the compounds of formula I can be administered in combination with more than one additional active agent, for example, a combination of a compound of formula I with an HMG-CoA reductase inhibitor (e.g. lovastatin, simvastatin and pravastatin) and aspirin, or a compound of formula I with an HMG-CoA reductase inhibitor and a beta blocker.

Another example of combination therapy can be seen in treating obesity or obesity-related disorders, wherein the compounds of formula I may be effectively used in combination with for example, fenfluramine, dexfenfluramine, phentiramine and β3 adrenergic receptor agonist agents.

Still another example of combination therapy can be seen in treating diabetes and related disorders wherein the compounds of formula I can be effectively used in combination with for example sulfonylureas, biguanides, α-glucosidase inhibitors, other insulin secretogogues, insulin as well as the active agents discussed above for treating atherosclerosis.

In accordance with this invention, a pharmaceutically effective amount of a compound of formula I can be used for the preparation of a medicament useful for treating diabetes, treating obesity, lowering tryglyeride levels, raising the plasma level of high density lipoprotein, and for treating, preventing or reducing the risk of developing atherosclerosis, and for preventing or reducing the risk of having a first or subsequent atherosclerotic disease event in mammals, particularly in humans.

Additionally, an effective amount of a compound of formula I and a therapeutically effective amount of one or more active agents selected from the group consisting of: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozol; vitamin $B_6$ and the pharmaceutically acceptable salts thereof; vitamin $B_{12}$; an antioxidant vitamin; a beta-blocker; an angiotensin II antagonist; an angiotensin converting enzyme inhibitor; a platelet aggregation inhibitor; a fibrinogen receptor antagonist; aspirin; fenfluramines, dexfenfluramines, phentiramines, β3 adrenergic receptor agonists; sulfonylureas, biguanides, α-glucosidase inhibitors, other insulin secretogogues, and insulin can be used together for the preparation of a medicament useful for the above-described treatments.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Specific examples of formula I may require the use of protecting groups to enable their successful elaboration into the desired structure. Protecting groups may be chosen with reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butldiphenyisilyl, 2-(trimethylsilyl)ethyl, phenacyl, p-methoxybenzyl, acetonyl, p-methoxyphenyl, 4-pyridylmethyl and t-butyl.

The compounds used in the method of the invention can be prepared readily according in the following detailed examples using readily available starting materials, reagents and conventional systhesis procedures. In these reactions, it is also possible to make use of variants which are themselves known to those of ordinary skill in this art, but which are not mentioned in greater detail. Additional background information and further details on the preparation of the compounds of formula XI and XII is taught in EP B-106565, the entire disclosure of which is incorporated herein by reference.

EXAMPLE 1

4-(3-(4-Acetyl-3-hydroxy-2-propylphenoxy) propylthio) 2,3-dichlorobenzeneacetic Acid Step A. Preparation of 2,3-dichloro-4-methoxy-acetophenone To a suspension of $AlCl_3$, 80 gm, in $CH_2Cl_2$, 1000 mL, was added dropwise acetyl-chloride, 31.6 gm. The solution was cooled at −5° C. and 2,3-dichloroanisole, 70.8 gm, dissolved in $CH_2Cl_2$, 50 mL, was then added. The solution was allowed to warm to room temperature and was stirred for 4 hours. The reaction mixture was poured on ice and stirred for 30 minutes. The organic layer was decanted and the aqueous layer was extracted with $CH_2Cl_2$. The combined fractions were washed with brine, dried ($Na_2SO_4$) and concentrated to a small volume. The addition of hexane caused crystallization of the title compound that was filtered to yield 57.7 gm (66%), mp 73°–77° C., analysis, calculated: C, 49.34; H, 3.68; Cl, 32.36; obtained: C, 49.09; H, 3.61; Cl, 32.34.

Step B: Preparation of 2,3-dichloro-4-methoxybenzene acetic acid, methyl Ester

To a mixture of 2,3-dichloro-4-methoxyacetophenone, 58 gm, methanol, 450 mL, and 70% perchloric acid, 88 mL, cooled to 0° C., there was added thallium trinitrate trihydrate, 117 gm. The reaction mixture was allowed to warm to room temperature and was stirred for 18 hours. The mixture was poured in water, 700 mL, and was extracted twice with $CH_2Cl_2$, 500 mL. The combined organic fractions were washed successively with water, 5% $NaHCO_3$ and with water, dried ($Na_2SO_4$) and concentrated in vacuo to yield, after purification by chromatography on silica gel, the title compound, 50.6 gm, as an oil, readily characterized by its NMR spectrum: (ppm) ($CDCl_3$) 3.85 (3H, s, $CH_3O$), 3.73 (2H, s, $CH_2CO$), 3.68 (3H, s, $CH_3O$).

Step C: Preparation of 2,3-dichloro-4-hydroxy-benzeneacetic acid, methyl Ester.

2,3-Dichloro-4-methoxybenzeneacetic acid, methyl ester, 46 gm, was refluxed for 18 hours in concentrated HBr, 350 mL. The reaction mixture was poured in water, 1.4 L, and the solution was extracted with EtOAc, 2×500 mL. The organic layers were washed with water, dried ($Na_2SO_4$) and concentrated to dryness. The residue was slurried in 20% EtOAc-hexane to yield 2,3-dichloro-4-hydroxybenzeneacetic acid, mp 189°–190° C. The acid was stirred at room temperature in methanolic HCl, 100 mL, for 30 minutes. The volatiles were removed in vacuo and the residue was slurried in hexane, filtered and air-dried to yield 17.6 gm of the title compound, mp 105°–106° C., analysis, calculated: C, 45.98; H, 3.43; Cl, 30.16; obtained: C, 46.10; H, 3.65; Cl, 30.31.

Step D: Preparation of 2,3-dichloro-4-dimethyl-thiocarbamoyloxybenzeneacetic acid, methyl ester Sodium hydride, 99%, 1.3 gm, was added to a solution of 2,3-dichloro-4-hydroxybenzeneacetic acid, methyl ester, 11.4 gm, in DMF, 100 mL. The mixture was stirred until evolution of $H_2$ gas subsided. Dimethylthiocarbamoyl chloride, 6.5 gm, was then added and the reaction mixture was stirred at room temperature for 18 hours. The reaction mixture was poured in water, 200 mL, and was extracted with ether, 500 mL. The ether layer was washed with water, dried ($Na_2SO_4$) and concentrated in vacuo to yield an oil that was purified by chromatography on silica gel to yield 11.7 gm of the title compound, mp 87°–93° C., analysis, calculated: C, 44.73; H, 4.06; N, 4.34; S, 9.95; Cl, 22.00; obtained: C, 44.44; H, 4.15; N, 4.05; S, 9.05; Cl, 21.65.

Step E: Preparation of 2,3-dichloro-4-dimethyl-carbamoylthiobenzeneacetic acid, methyl Ester 2,3 -Dichloro-4-dimethylthiocarbamoylbenzene-acetic acid, methyl ester, 10.7 gm, was heated under $N_2$ atmosphere at 250° C. for 30 minutes. The reaction mixture was cooled to room temperature and after a purification by chromatography on silica gel, the title compound, 6.8 gm, was obtained, mp 119°–122° C., analysis, calculated: C, 44.73; H, 4.06; N, 4.34; S, 9.95; Cl, 22.00; obtained: C, 44.50; H, 4.21; N, 4.25; S, 10.19; Cl, 22.57.

Step F: Preparation of the sodium salt of 2,3-dichloro-4-mercaptobenzeneacetic acid, methyl Ester 2,3-Dichloro-4-dimethylcarbamoylthiobenzene-acetic acid, methyl ester, 3.22 gm, was refluxed in methanol, 60 mL, containing sodium methoxide, 855 mg, for 1 hour. The reaction mixture, containing about 10 millimoles of the sodium salt of the title compound, in 60 mL MeOH, was used as such in Step G.

Step G: Preparation of 4-(3-(4-acetyl-3-hydroxy-2-propylphenoxy)propylthio)-2,3 -dichlorobenzene-acetic acid, methyl Ester To 30 mL of the solution obtained in Step F was added 4-(3-bromopropoxy)-3-propyl-2-hydroxyacetophenone, 1.73 gm, and the reaction mixture was refluxed for 2 hours. It was then poured in water and extracted with EtOAc. The extract was washed with water, dried ($Na_2SO_4$) and concentrated in vacuo. The title compound, mp 82°–85° C. was obtained by chromatography of the residue on silica gel.

Step H: Preparation of 4-(3-(4-acetyl-3-hydroxy-2-propylphenoxy)propylthio)-2,3-dichloro-benzeneacetic acid The ester prepared in Step F, 964 mg, dissolved in 1N NaOH, 10 mL, and in methanol, 30 mL, was refluxed for 30 minutes. The volatiles were evaporated in vacuo. The residue was taken up in water and the resulting solution was acidified with 20% citric acid. The mixture was extracted with EtOAc, the extracts were washed with water, dried ($Na_2SO_4$) and concentrated in vacuo to yield the title compound, mp 119°–122° C.

EXAMPLE 2

4-(3-(4-Acetyl-3-hydroxy-2-propylphenoxy)-2-hydroxy-propylthio)-2,3-dichlorobenzeneacetic Acid Step A: Preparation of 4-(3-(4-acetyl-3-hydroxy-2-propylphenoxy)-2-hydroxypropylthio)-2,3-dichlorobenzeneacetic acid, methyl Ester By following Step G of Example 1, but substituting 4-(2,3 epoxypropoxy)-3-propyl-2-hydroxy- acetophenone for 4-(3-bromopropoxy)-3-propyl-2-hydroxyacetophenone, the title compound, mp 85°–88° C., was obtained.

Step B: 4-(3-(4-acetyl-3-hydroxy-2-propylphenoxy)-2-hydroxypropylthio)-2,3-dichlorobenzeneacetic Acid By following Step H of Example 1, but substituting the product of Step A of this example for the ester of Step G of Example 1, the title compound, mp 151°–153° C., was obtained.

EXAMPLE 3

4-(3-(4-Acetyl-3-hydroxy-2-propylphenoxy) propylthio)-2,3-dichlorobenzeneacetic acid-S-Oxide Step A: Preparation of 4-(3-(4-acetyl-3-hydroxy-2-propylphenoxy)propylthio)-2,3-dichlorobenzene-acetic acid-S-oxide, methyl Ester The product obtained in Step G of Example 1, 1.4 gm, in $CH_2Cl_2$, 35 mL, was treated with m-chloroperbenzoic acid, 560 mg, for 15 minutes at 0° C. $Ca(OH)_2$, 3 gm, was added and the resulting suspension was stirred for 10 minutes. The solids were filtered off and the filtrate was concentrated in vacuo to yield the title compound, mp 153°–155° C.

Step B: Preparation of 4-(3-(4-acetyl-3-hydroxy-2-propylphenoxy)propylthio)-2,3-dichlorobenzene-acetic acid-S-Oxide By following Step H of Example 1, but substituting the product of Step A of this example for the ester of Step G of Example 1, the title compound, mp 162°–164° C., was obtained.

EXAMPLE 4

4-(3-(4-Acetyl-3-hydroxy-2-propylphenoxy)propyl-sulfonyl)-2,3-dichlorobenzeneacetic Acid Step A: Preparation of 4-(3-(4-acetyl-3-hydroxy-2-propylphenoxy)propylsulfonyl)-2,3 -dichloro-benzeneacetic acid, methyl Ester The product obtained in Step G of Example 1, 1.4 gm, in $CH_2Cl_2$, 35 mL, was treated with m-chloroperbenzoic acid, 1.15 gm, for 2 hours at room temperature. $Ca(OH)_2$, 4 gm, was added and the resulting suspension was stirred for 10 minutes. The solids were filtered off and the filtrate was concentrated in vacuo to yield the title compound, mp 115°–118° C.

Step B: Preparation of 4-(3-(4-acetyl-3-hydroxy-2-propylphenoxy)propylsulfonyl)-2,3-dichloro-benzeneacetic Acid By following Step H of Example 1, but substituting the product of Step A of this example for the ester of Step G of Example 1, the title compound, mp 180°–181° C., was obtained.

EXAMPLE 5

4-(3-(4-Acetyl-3-hydroxy-2-propylphenoxy)-2-hydroxy-propylthio)-2,3-dichlorobenzeneacetic acid-S-Oxide Step A: Preparation of 4-(3-(4-acetyl-3-hydroxy-2-propylphenoxy)-2-hydroxypropylthio)-2,3-dichlorobenzeneacetic acid-S-oxide, methyl Ester By following Step A of Example 3, but substituting the product of Step A of Example 2 for the ester of Step G of Example 1, the title compound, mp 149°–152° C., was obtained.

Step B: Preparation of 4-(3-(4-acetyl-3-hydroxy-2-propylphenoxy)-2-hydroxypropylthio)-2,3-dichlorobenzeneacetic acid-S-Oxide By following Step H of Example 1 but substituting the product of Step A of this example for the ester of Step G of Example 1, the title compound, mp 166°–170° C., was obtained.

EXAMPLE 6

4-(3-(4-Acetyl-3-hydroxy-2-propylphenoxy)-2-hydroxy-propylsulfonyl)-2,3-dichlorobenzeneacetic Acid Step A: Preparation of 4-(3-(4-acetyl-3-hydroxy-2-propylphenoxy)-2-hydroxypropylsulfonyl)-2,3-dichlorobenzeneacetic acid, methyl Ester By following Step A of Example 4, but substituting the product of Step A of Example 2 for the ester from Step G of Example 1, the title compound, mp 122°–125° C., was obtained.

Step B: Preparation of 4-(3-(4-acetyl-3-hydroxy-2-propylphenoxy)-2-hydroxypropylsulfonyl)-2,3-dichlorobenzeneacetic Acid By following Step H of Example 1, but substituting the product from Step A of this example for the ester of Step G of Example 1, the title compound, mp 181°–183° C., was obtained.

EXAMPLE 7

4-(3-($^4$-Acetyl-3-hydroxy-2-propylphenoxy) propylthio-2-fluorobenzeneacetic Acid Step A: Preparation of 4-methoxy-2-Fluoroacetophenone By following Step A of Example 1, but substituting m-fluoroanisole for 2,3-dichloroanisole, the title compound, mp 50°–52° C., was obtained.

Step B: Preparation of 4-methoxy-2-fluorobenzene-acetic acid, methyl Ester

By following Step B of Example 1 but substituting 4-methoxy-2-fluoroacetophenone for 2,3-dichloro-4-methoxyaceto-phenone, the title compound, bp 112°–115° C./1 Torr, was obtained.

Step C: Preparation of 4-hydroxy-2-fluorobenzene acetic acid. methyl Ester

By following Step C of Example I but substituting 4-methoxy-2-fluorobenzeneacetic acid, methyl ester for 2,3-dichloro-4-methoxybenzeneacetic acid, methyl ester, 4-hydroxy-2-fluorobenzeneacetic acid was obtained as a sticky solid which was treated with methanolic HCl to yield the title compound as anoil. It was characterized by its NMR spectrum: (ppm) (CDCl$_3$) 3.70 (3H, s, CH$_3$O), 3.55 (2H, s, CH$_2$).

Step D: Preparation of 2-fluoro-4-dimethylthio-carbamoyloxybenzeneacetic acid, methyl Ester By following Step D of Example 1 but substituting 4-hydroxy-2-fluorobenzeneacetic acid, methyl ester for 4-hydroxy-2,3-dichlorobenzeneacetic acid, methyl ester, the title compound, mp 113°–114° C., was obtained.

Step E: Preparation of 2-fluoro-4-dimethyl-carbamoylthiobenzeneacetic acid, methyl Ester By following Step E of Example 1 but substituting 2-fluoro-4-dimethylthiocarbamoyloxy-benzeneacetic acid, methyl ester for 2,3-dichloro-4-dimethylthiocarbamoyloxybenzeneacetic acid, methyl ester, the title compound, mp 79°–81° C., was obtained.

Step F: Preparation of the sodium salt of 2-fluoro-4-mercaptobenzeneacetic acid, methyl Ester By following Step F of Example 1 but substituting 2-fluoro-4-dimethylcarbamoylthiobenzene-acetic acid, methyl ester for 2,3-dichloro-4-dimethyl-carbamoylthiobenzeneacetic acid, methyl ester a solution of the title compound was obtained and was used as such in the following Step.

Step G: Preparation of 4-(3-(4-acetyl-3-hydroxy-2-propylphenoxy)propylthio-2-fluorobenzene-acetic acid, methyl Ester By following Step G of Example 1 but substituting the product of Step F of this example for the product of Step F of Example 1, the title compound, mp 63°–65° C., was obtained.

Step H: Preparation of 4-(3-(4-acetyl-3-hydroxy-2-propylphenoxy)propylthio-2-fluorobenzene-acetic Acid By following Step H of Example 1, but substituting the methyl ester of Step G of this example for the methyl ester of Step G of Example 1, the title compound, mp 154°–156° C., was obtained.

EXAMPLE 8

Sodium Salt of 4-(3-(4-Acetyl-3-hydroxy-2-propyl-phenoxy)-2-hydroxypropylthio-2-fluorobenzeneacetic acids Monohydrate Step A: Preparation of 4-(3-(4-acetyl-3-hydroxy-2-propylphenoxy)-2-hydroxypropylthio-2-fluoro benzeneacetic acid, methyl Ester By following Step G of Example 7, but substituting 4-(2,3-epoxypropoxy)-3-propyl-2-hydroxy-acetophenone for 4-(3-bromopropoxy)- 3-propyl-2-hydroxyacetophenone, the title compound was obtained as an oil. Analysis, calculated: C, 61.31; H, 6.04; F, 4.21; S, 7.11; obtained: C, 61.08; H, 6.51; F, 3.93; S, 6.69.

Step B: Preparation of the sodium salt of 4-(3-(4-acetyl-3-hydroxy-2-propylphenoxy)-2-hydroxy-propylthio-2-fluorobenzeneacetic acid, Monohydrate By following Step H of Example 7, but substituting the product of Step A of this example for the ester of Step G of Example 7, the corresponding acid of the title compound was obtained as an oil. It was treated with one equivalent of sodium hydroxide in water to yield, after evaporation of the water, the title compound, mp 75°–83° C., analysis, calculated: C, 55.45; H, 5.50; F, 3.98; S, 6.73; obtained: C, 55.55; H, 5.56; F, 4.71; S, 6.99.

EXAMPLE 9

4-(3-(4-Acetyl-3-hydroxy-2-propylphenoxy)-2-hydroxy-propylthio)-2-fluorobenzeneacetic acid-S-Oxide Step A: Preparation of 4-(3-(4-acetyl-3-hydroxy-2-propylphenoxy)-2-hydroxypropylthio)-2-fluoro-benzeneacetic acid-S-oxide, methyl Ester By following Step A of Example 3, but substituting the title compound of Step A of Example 8 for the title compound of Step G of Example 1, the title compound is obtained.

Step B: Preparation 4-(3-(4-acetyl-3-hydroxy-2-propylphenoxy)-2-hydroxypropylthio)-2-fluorobenzeneacetic acid-S-Oxide By following Step H of Example 2, but substituting the product of Step A of this example for the ester of Step G of Example 1, the title compound is obtained.

EXAMPLE 10

4-(3-(4-Acetyl-3-hydroxy-2-propylphenoxy)-2-hydroxy-propylsulfonyl)-2-fluorobenzeneacetic acid; and 4-(3-(4-Acetyl-3-hydroxy-2-propylphenoxy)-1-propenyl-sulfonyl)-2-fluorobenzeneacetic Acid Step A: Preparation of 4-(3-(4-acetyl-3-hydroxy-2-propylphenoxy)-2-hydroxypropylsulfonyl)-2-fluorobenzeneacetic acid, methyl Ester By following Step A of Example 4, but substituting the product of Step A of Example 8 for the title compound of Step G of Example 1, the title compound, mp 118°–119° C., was obtained.

Step B: Preparation of 4-(3-(4-acetyl-3-hydroxy-2-propylphenoxy)-2-hydroxypropylsulfonyl)-2-fluorobenzeneacetic acid; and 4-(3-(4-acetyl-3-hydroxy-2-propylphenoxy)-1-propenylsulfonyl)-2-fluorobenzeneacetic Acid By following Step H of Example 1, but substituting the product of Step A of this example for the ester of Step G of Example 1, a mixture was obtained. After recrystallization from diethyl ether, 4-(3-(4-acetyl-3-hydroxy-2-propylphenoxy)-2-hydroxypropylsulfonyl)-2-fluorobenzeneacetic acid, mp 119°–120° C., was obtained. The mother liquors were purified by chromatography on silica gel to yield 4-(3-(4-acetyl-3-hydroxy-2-propylphenoxy)-1-propenyl-sulfonyl)-2-fluoro-benzene acetic acid, mp 249°–251° C.

BIOLOGICAL ASSAYS

The ability of compounds of the present invention to enhance the insulin activation of $^{14}C$-glucose incorporation into glycogen in white adipose tissue (WAT) was determined by the following assay.

Biological Assays
I. White Adipose Tissue in vitro Assay

The ability of compounds of the present invention to enhance the insulin activation of $^{14}C$-glucose incorporation into glycogen in white adipose tissue (WAT) was determined by the following assay.

This assay measures the efficacy of the instant compounds to enhance the insulin activation of $^{14}C$-glucose incorporation into glycogen in white adipose tissue (WAT) in a 5 hour completely in vitro system. All procedures are performed in medium 199 containing 1% bovine serum albumen, 5 mM HEPES, and antibiotic (100 units/ml penicillin, 100 µg/ml streptomycin sulfate, 0.25 µg/ml amphotericin B), hereafter called culture medium. Epididymol fat pads are minced with scissors into small fragments, approximately 1 mm in diameter. Minced WAT fragments (100 mg) are incubated in a total volume of 0.9 ml culture medium containing 1 mU/ml insulin and test compound in tissue culture incubator at 37° C. with 5% $CO_2$ with orbital shaking for 3 hours. $^{14}C$-labeled glucose is added and incubation continued for 2 hours. Tubes are centrifuged at low speed, infranatant is removed and 1M NaOH is added. Incubation of alkali-treated WAT for 10 minutes at 60° C. solubilizes tissue. Resulting tissue hydrolyzate is applied to Whatman filter paper strips which are then rinsed in 66% ethanol followed by 100% acetone which removes unincorporated $^{14}C$-glucose from bound $^{14}C$-glycogen. The dried paper is then incubated in solution of amyloglucosidase to cleave glycogen into glucose. Scintillation fluid is added and samples are counted for $^{14}C$ activity. Test compounds that resulted in $^{14}C$ activity substantially above incubations with insulin alone are considered active insulin-enhancing agents. Active compounds were titrated to determine the compound concentration which resulted in 50% of maximum enhancement of insulin activation and were termed $EC_{50}$ values. $EC_{50}$ values for the instant compounds were found to be 50 µM or less, preferably 5.0 to 0.0001 µM or less.

II. PPAR Receptor Binding and/or Transactivation Assays

Compounds of the instant invention which are useful for the above discussed treatments can be identified and/or characterized by employing the PPAR δ, and γ binding assays and/or PPAR δ, PPAR α and PPARγ transactivation assays. The assays are useful in predicting or quantitating in vivo effects having to do with the control or modulation of glucose, free fatty acid, triglyceride, insulin or cholesterol. To evaluate $IC_{50}$ or $EC_{50}$ values the compounds were titrated in the appropriate assay using different concentrations of the compound to be tested. To obtain the appropriate values (%Inhibition-$IC_{50}$, or %Activation-$EC_{50}$), the data resulting from the assays were then analyzed by determining the best fit of a 4 parameter function to the data using the Levenberg-Marquardt non-linear fitting algorithm in Kaleidagraph (Synergy Software, Reading, Pa.). The human nuclear receptor cDNA for PPARδ (hPPARδ) has been cloned from a human osteosarcoma cell cDNA library and is fully described in A. Schmidt et al., Molecular Endocrinology, 6:1634–1641 (1992), herein incorporated by reference in its entirety. See A. Elbrecht et al., Biochem. and Biophy. Res. Comm. 224:431–437 (1996) and T. Sher et al., Biochem. 32:5598–5604 (1993) for a description of the human nuclear receptor gene PPARγ and α.

The hPPARδ binding assay comprises the steps of:
(a) preparing multiple test samples by incubating separate aliquots of the receptor hPPARδ with a test compound in TEGM containing 5–10% COS-1 cell cytoplasmic lysate and 2.5 nM labeled ([$^3H_2$]Compound D, 17 Ci/mmole) for a minimum of 12 hours, and preferably for about 16 hours, at 4 ° C., wherein the concentration of the test compound in each test sample is different, and preparing a control sample by incubating a further separate aliquot of the receptor hPPARδ under the same conditions but without the test compound; then
(b) removing unbound ligand by adding dextran/gelatin-coated charcoal to each sample while maintaining the samples at 4 ° C. and allowing at least 10 minutes to pass, then
(c) subjecting each of the test samples and the control sample from step (b) to centrifugation at 4 ° C. until the charcoal is pelleted; then
(d) counting a portion of the supernatant fraction of each of the test samples and the control sample from step (c) in a liquid scintillation counter and analyzing the results to determine the $IC_{50}$ of the test compound.

In the hPPARδ binding assay, preferably at least four test samples of varying concentrations of a single test compound are prepared in order to determine the $IC_{50}$.

The hPPARδ transactivation assay comprises the steps of:
(a) seeding an hPPARδ/GR stable CHO-K1 cell line into alpha MEM containing 10% FCS, 10 mM HEPES, and 500 mg/ml G418 at 37° C. in an atmosphere of 10% $CO_2$ in air, (b) incubating the cells from step (a) for 16 to 48 hours, preferably about 20 hours, at 37° C. in an atmosphere of 10% $CO_2$ in air;

(c) washing the cells from step (b) with alpha MEM;

(d) preparing multiple test cell groups by incubating separate groups of the cells from step (c) with the test compound in alpha MEM containing 5% charcoal stripped FCS, 10 mM HEPES, and 500 mg/ml G418, for 24 to 48 hours, preferably about 24 hours, at 37° C. in an atmosphere of 10% $CO_2$ in air, wherein the concentration of the test compound in each test cell group is different, and preparing a control cell group by incubating a further separate group of the cells from step (c) under the same conditions but without the test compound; then (e) preparing cell lysates from each of the test cell groups and the control cell group of step (d) using an aqueous detergent lysis buffer, and (f) measuring the luciferase activity of the test cell groups and the control cell group of step (e) and analyzing the results to determine the $EC_{50}$ of the test compound.

In the hPPARδ transactivation assay, preferably at least four test cell groups of varying concentrations of a single test compound are prepared in order to determine the $EC_{50}$.

Particular terms and abbreviations used herein are defined as follows: gst is glutathione-S-transferase; EDTA is ethylenediamine-tetraacetic acid; HEPES is N-[2-hydroxyethyl]-piperazine-N'-[2-ethanesulfonic acid]; FCS is fetal calf serum; Lipofectamine is a 3:1 (w/w) liposome formulation of the polycationic lipid 2,3-dioleyloxy-N-[2 (spermine-carboxamido)ethyl]-N,N-dimethyl-1 -propanaminium-trifluoroacetate and the neutral lipid dioleoyl phosphatidylethanolamine in water; G418 is geneticin; MEM is Minimum Essential Medium; Opti MEM 1 Reduced-Serum Medium is an aqueous composition containing HEPES buffer, 2400 mg/L sodium bicarbonate, hypoxanthine, thymidine, sodium pyruvate, L-glutamine, trace elements, growth factors, and phenol red reduced to 1.1 mg/L; Luciferase Assay Reagent (in re-constituted form) is an aqueous composition containing 20 mM tricine, 1.07 mM $(MgCO_3)_4Mg(OH)_2 \cdot 5H_2O$, 2.67 mM $MgSO_4$, 0.1 mM EDTA, 33.3 mM DTT, 270 μM coenzyme A, 470 μM luciferin, 530 μM ATP, having a final pH of 7.8.

AD-5075 has the following structure:

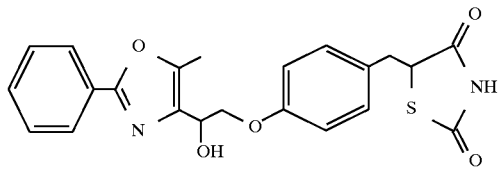

AD-5075 (Takeda)

Opti MEM 1 Reduced-Serum Medium, alpha MEM, G418, and Lipofectamine are commercially available from GibcoBRL Life Technologies, Gaithersburg, Md. Alpha MEM is an aqueous composition having the following components:

| Component: Inorganic Salts | mg/L |
|---|---|
| $CaCl_2$ (anhyd.) | 200.00 |
| $CaCl_2 \cdot 2H_2O$ | — |
| KCl | 400.00 |

-continued

| | mg/L |
|---|---|
| $MgSO_4$ (anhyd.) | 97.67 |
| $MgSO_4 \cdot 7H_2O$ | — |
| NaCl | 6800.00 |
| $NaHCO_3$ | 2200.00 |
| $NaH_2PO_4 \cdot H_2O$ | 140.00 |
| $NaH_2PO_4 \cdot 2H_2O$ | — |
| Other Components: | |
| D-Glucose | 1000.00 |
| Lipoic Acid | 0.20 |
| Phenol Red | 10.00 |
| Sodium Pyruvate | 110.00 |
| Amino Acids: | |
| L-Alanine | 25.00 |
| L-Arginine.HCl | 126.00 |
| L-Asparagine.$H_2O$ | 50.00 |
| L-Aspartic Acid | 30.00 |
| L-Cystine | — |
| L-Cystine.2HCl | 31.00 |
| L-Cysteine HCl | — |
| L-Cysteine HCl.$H_2O$ | 100.00 |
| L-Glutamic Acid | 75.00 |
| L-Glutamine | 292.00 |
| L-Alanyl-L-Glutamine | — |
| Glycine | 50.00 |
| L-Histidine HCl.$H_2O$ | 42.00 |
| L-Isoleucine | 52.00 |
| L-Leucine | 52.00 |
| L-Lysine.HCl | 73.00 |
| L-Methionine | 15.00 |
| L-Phenylalanine | 32.00 |
| L-Proline | 40.00 |
| L-Serine | 25.00 |
| L-Threonine | 48.00 |
| L-Tryptophan | 10.00 |
| L-Tyrosine | — |
| L-Tyrosine (disodium salt) | 52.00 |
| L-Valine | 46.00 |
| Vitamins: | |
| L-Ascorbic acid | 50.00 |
| Biotin | 0.10 |
| D-Ca Pantothenate | 1.00 |
| Choline Chloride | 1.00 |
| Folic acid | 1.00 |
| i-Inositol | 2.00 |
| Niacinamide | 1.00 |
| Pyridoxal HCl | 1.00 |
| Riboflavin | 0.10 |
| Thiamine HCl | 1.00 |
| VitaminB$_{12}$ | 1.40 |
| Ribonucleosides | |
| Adenosine | 10.00 |
| Cytidine | 10.00 |
| Guanosine | 10.00 |
| Uridine | 10.00 |
| Deoxyribonucleosides | |
| 2' Deoxyadenosine | 10.00 |
| 2' Deoxycytidine HCl | 11.00 |
| 2' Deoxyguanosine | 10.00 |
| Thymidine | 10.00 |

The instant compounds, which are useful for treating the above discussed disease states, will preferably have $IC_{50}$ values at one, two or all of the PPAR (PPARγ, PPARδ or PPARα) receptor cites of equal to or less than 10 μM binding assay, and an $EC_{50}$ equal to or less than 10 μM in the transactivation assay. Preferably, an $IC_{50}$ of 100 nM in the binding assay, and an $EC_{50}$ equal to or less than 100 nM in the transactivation assay. More preferably, the instant compounds have an $IC_{50}$ equal to or less than 50 nM in the binding assay, and an $EC_{50}$ equal to or less than 50 nM in the transactivation assay. Most preferably, the instant compounds have an $IC_{50}$ equal to or less than 10 nM in the binding assay, and an $EC_{50}$ equal to or less than 10 nM in the transactivation assay.

PPAR Receptor Binding Assay

A. Preparation of Human PPARγ2 and δ

Human PPARγ2 and PPARδ, independently, were prepared as gst-fusion proteins in *E. coli*. The full length human cDNA for PPARγ2 and PPARδ were subcloned into the PGEX-2T and PGEX-KT, respectively, expression vector (Pharmacia). *E. coli* containing the plasmid were grown, induced, and then harvested by centrifugation. The resuspended pellet was broken in a French press and debris was removed by centrifugation at 12,000×g. Receptors were purified from the supernatant by affinity chromatography on glutathione sepharose. After application to the column, and 1 wash, receptor was eluted with glutathione. Glycerol was added to stabilize the receptor and aliquots were frozen at −80 °C. for later use.

B. [$^3$H]AD-5075 and Example 11 Displacement Assay for PPARγ2 and PPARδ, Respectively For each assay, an aliquot of receptor (1:1000–1:3000 dilution) was incubated in TEGM (10 mM Tris, pH 7.2, 1 mM EDTA, 10% glycerol, 7 μl/100 ml β-mercaptoethanol, 10 nM Na molybdate, 1 mM dithiothreitol, 5 μg/ml aprotinin, 2 μg/ml leupeptin, 2 μg/ml benzamide and 0.5 mM PMSF) containing 5–10% COS-1 cell cytoplasmic lysate and 10 nM labeled thiazolidinedione ([$^3$H$_2$]AD-5075, 21 Ci/mmole), ±test compound compound, [$^3$H$_2$]Example 11, 17 Ci/mmole), ±test compound, respectively. Assays were incubated for ~16 h at 4 °C. in a final volume of 300 μl. Unbound ligand was removed by addition of 200 μl dextran/gelatin-coated charcoal, on ice, for ~10 minutes. After centrifugation at 3000 rpm for 10 min at 4° C., 200 μl of the supernatant fraction was counted in a liquid scintillation counter. In this assay the KD for AD-5075 and Example 11 is 1 nM, respectively.

PPAR Receptor Transactivation Assay

A. Activation of hPPARγ and hPPARδMethods

1. Plasmids

The chimeric receptor expression constructs, pSG5-hPPARγ2/GR and pSG5-hPPARδ/GR, were prepared by inserting the DNA binding domain of the murine glucocorticoid receptor adjacent to the ligand binding domain of hPPARγγ or hPPARδ. These vectors were kindly provided by Dr. Azriel Schmidt (MRL). The glucocorticoid receptor-responsive reporter vector, pMMTV/luc/neo, contains the murine mammary tumour virus (MMTV) promoter adjacent to the luciferase gene (luc) and the neomycin resistance gene (neo). It was constructed from pMMTV/luc which was provided by Dr. Azriel Schmidt (Merck Research Laboratories). Prior to transfection into CHO-K1 cells, pSG5-hPPARγ2/GR and pSG5-hPPARδ/GR were linearized with Xba I. pMMTV/luc/neo DNA was cut with Pvu I. Wild type receptor constructs, pSG5-hPPARγ2, pSG5-hPPARδ and pSG5-hPPARα were prepared by inserting the full-length hPPARγ2, hPPARδand PPARα cDNAs adjacent to the SV40 promoter in pSG5. The PPAR-responsive reporter construct, pPPRE-luc, contained 3 copies of a generic PPRE placed adjacent to the thymidine kinase minimal promoter and the luciferase reporter gene. The transfection control vector, pCMV-lacZ, contains the galactosidase Z gene under the regulation of the cytomegalovirus promoter.

2. Production of Stable Cell Lines

CHO-K1 cells were seeded overnight at 6×10$^5$ cells /60 mm dish in alpha Minimum Essential Medium (MEM) containing 10% fetal calf serum (FCS), 10 mM HEPES, 100 units/ml PenicillinG and 100 μug/ml Streptomycin sulfate at 37° C. in an atmosphere of 10% $CO_2$ in air. The cells were washed once with OptiMEM 1 Reduced-Serum Medium and then cotransfected with 4.5 μg of pSG5-hPPARγ2 /GR or pSG5-hPPARδ/GR expression vector and 0.5 μg of pMMTV/luc/neo in the presence of 100 μg Lipofectamine (GIBCO BRL) according to the instructions of the manufacturer. Transfection medium was removed 2 h later and replaced with growth medium. After being incubated for 3 days, cells were subcultured by diluting the cell suspension 1/1250 and 1/6250 and placing the cells in a 100 mm culture dish. Selection of the stable cell lines was initiated the next day by adding 500 μg/ml G418 to the medium. Cells were routinely fed with the selection media for 1 month at which time 120 colonies were picked and transferred to 24 well culture plates. Ten days later, confluent colonies were transferred to 6 well plates to maintain stocks and to 96 well plates to assay for luciferase activity. Positive clones were characterized and validated by titrating 4 known agonists on each clone. Two clones, g2B2P2D9 and d2A5P2G3, were selected for screening purposes.

B. hPPAR/GR Transactivation Screens in Stably Transfected CHO-K1 Cells

The hPPARγ2/GR and hPPARδ/GR stable CHO-K1 cell lines were seeded at 1×10$^4$ cells/well in 96 well cell culture plates in alpha MEM containing 10% FCS, 10 mM HEPES, and 500 mg/ml G418 at 37° C. in an atmosphere of 10% $CO_2$ in air. After a 20 hour incubation, cells were washed once with alpha MEM and then incubated in an atmosphere of 10% $CO_2$ in air in alpha MEM containing 5% charcoal stripped FCS, 10 mM HEPES, and 500 mg/ml G418. The cells were incubated for 24 hours in the absence of test compound or in the presence of a range of concentrations of test compound. Cell lysates were prepared from washed cells using Reporter Lysis Buffer (Promega) according to the manufacturer's directions. Luciferase activity in cell extracts was determined using Luciferase Assay Reagent buffer (Promega) in a ML3000 luminometer (Dynatech Laboratories).

Transactivation Wild-Type Assay

A. Characterization of Ligand Activity on Wild-Type hPPARγ, hPPARδ and hPPARα.

COS-1 cells were seeded at 0.5×10$^5$ cells/dish into 24 well plates in Dulbecco's modified Eagle medium (high glucose) containing 10% charcoal stripped fetal calf serum, nonessential amino acids, 100 units/ml Penicillin G and 100 μg/ml Streptomycin sulfate at 37° C. in a humidified atmosphere of 10% $CO_2$. After 24 hours, transfections were performed with Lipofectamine (Gibco-BRL, Gaithersburg, Md.) according to the instructions of the manufacturer. In general, for transactivation experiments, transfection mixes contained 0.15 mg of hPPARγ2 hPPARα or hPPARδ expression vector, 0.15 mg of reporter vector pPPRE-luc and 0.001 mg of pCMV-lacZ as an internal control of transfection efficiency. Compounds demonstrating significant agonist activity in the above primary screen were further characterized by incubation with transfected cells for 48h across a range of concentrations. Luciferase activity was determined as described above.

In a similar manner, hPPARγ1 cDNA can be used in place of hPPARγ2 cDNA in the methods described in Example 5 to make the wild type receptor construct, pSG5-hPPARγ1.

III. In vivo Studies

Methods db/db Mice are obese, highly insulin resistant animals. The db locus has been shown to code for the leptin receptor. These animals are substantially hypertriglyceridemic and hyperglycemic.

Male db/db mice (10–11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose) ±test compound at the indicated dose. Drug suspensions were prepared daily. Plasma glucose, Cholesterol and triglyceride concentrations were determined from blood obtained by tail bleeds at 3–5 day intervals during the study period. Glucose, cholesterol and triglyceride, determinations were performed on a Boehringer Mannheim Hitachi 911 automatic analyzer (Boehringer Mannheim, Indianapolis, Ind.) using heparinized plasma diluted 1:5, or 1:6 (v/v) with normal saline. Lean animals were age-matched heterozygous mice maintained in the same manner. The instant compounds were found to lower triglyceride and glucose levels at a dose of about 100mg/kg, preferably a dose of about 10–50 mg/kg, when administered by oral gavage daily for a period of at least 5 days.

Lipoprotein analysis was performed on either serum, or EDTA treated plasma obtained by heart puncture from anesthetized animals at the end of the study. Apolipoprotein concentrations were determined by ELISA, and cholesterol particles were analyzed by FPLC, precipitation, or ultracentrifugation. Total liver RNA was prepared from tissue that had been frozen on liquid nitrogen at the time of euthanasia. Apolipoprotein mRNA was analyzed on Northern Blots using specific probes for mouse or rat proteins.

What is claimed is:

1. A method for the treatment or prevention of diabetes which comprises administering to a diabetic patient a pharmaceutically effective amount of a compound of formula XI or XII:

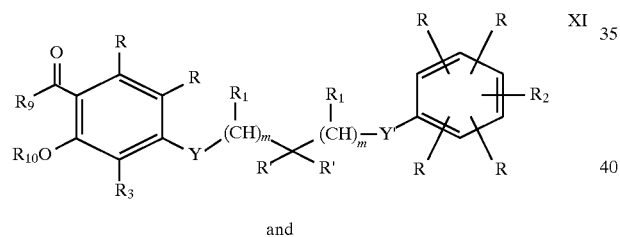

and

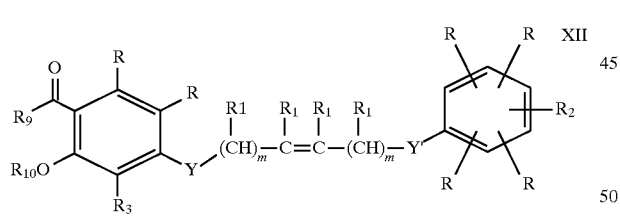

or a pharmaceutically acceptable salt or acid addition salt thereof, wherein:

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

Y' is sulfur, sulfoxide, sulfone;

$R_{11}$ is H, alkyl of 1–4 carbon atoms which may be straight chain or branched; alkanoyl of 1–4 carbon atoms which may be straight chain or branched; phenylsulfonyl; tosyl; $NR_{12}$ wherein $R_{12}$ is H, alkyl of 1–4 carbon atoms which may be straight chain or branched; or

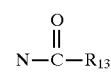

wherein $R_{13}$ is alkyl of 1–4 carbon atoms which may be straight chain or branched, alkoxy of 1–4 carbon atoms which may be straight chain or branched; N—CN, $CH_2$, or C=O;

Y is Y' and oxygen;

each $R_1$ is independently hydrogen or alkyl of 1–3 carbon atoms;

each m is independently an integer from 0–6;

$R_2$ is

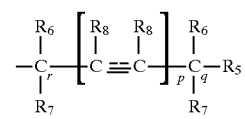

each $R_6$ is independently H or alkyl of 1–4 carbons;

each $R_7$ is independently H, OH, or alkyl of 1–4 carbons;

each $R_8$ is independently H, or alkyl of 1–4 carbons, and is absent when a triple bond is present;

$R_5$ is $COOR_4$; $CH_2OH$; CHO; tetrazole; $NHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is

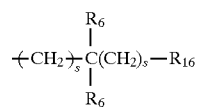

wherein each s is independently 0–3;

$R_{16}$ is

A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

$R_{14}$ is OH, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl, acyl of 1 to 6 carbon atoms or perfluoroalkyl of 1 to 4 carbon atoms;

r an q are each independently 0–20 provided that the total of r and q does not exceed 20;

p is 0 or 1;

$R_3$ is alkyl of 1 to 6 carbon atoms which may be straight chain or branched; or alkenyl of 3 to 6 carbon atoms which may be straight chain or branched as illustrated in formulas IV and V;

$R_9$ is alkyl of 1 to 6 carbon atoms which may be straight chain or branched; alkoxy of 1 to 6 carbon atoms which may be straight chain or branched; or $(CH_2)_rR_5$; and $R_{10}$ is H; alkyl of 1 to 6 carbon atoms which may be straight chain or branched;

$$R_4\overset{O}{\overset{\|}{C}}-$$

or $R_4OCH_2-$.

2. A method according to claim 1 wherein the compound is Y is oxygen and Y' is sulfur, sulfoxide, sulfone, amino or cyanamido.

3. A method according to claim 1 wherein each m is 1.

4. A method according to claim 1 wherein the compound is 4-(3-(4-Acetyl-3-hydroxy-2-propylphenoxy)propylthio)-2,3-dichlorobenzeneacetic acid and its methyl ester;

4-(3-(4-Acetyl-3-hydroxy-2-propylphenoxy)-2-hydroxypropylthio)-2,3-dichlorobenzeneacetic acid and its methyl ester;

4-(3-(4-Acetyl-3-hydroxy-2-propylphenoxy)propylthio)-2,3-dichlorobenzeneacetic acid-S-oxide and its methyl ester;

4-(3-(4-Acetyl-3-hydroxy-2-propylphenoxy)propylsulfonyl)-2,3-dichlorobenzeneacetic acid and its methyl ester;

4-(3-(4-Acetyl-3-hydroxy-2-propylphenoxy)-2-hydroxypropylthio)-2,3-dichlorobenzeneacetic acid-S-oxide and its methyl ester;

4-(3 -(4-Acetyl-3 -hydroxy-2-propylphenoxy)-2-hydroxy-propylthio)-2,3-dichlorobenzeneacetic acid-S-oxide and its methyl ester;

4-(3 -(4-Acetyl-3 -hydroxy-2-propylphenoxy)-2-hydroxy-propylsulfonyl)-2,3-dichlorobenzeneacetic acid and its methyl ester;

4-(3-(4-Acetyl-3-hydroxy-2-propylphenoxy)propylthio-2-fluorobenzeneacetic acid and its methyl ester;

Sodium Salt of 4-(3-(4-Acetyl-3-hydroxy-2-propylphenoxy)-2-hydroxypropylthio-2-fluorobenzeneacetic acid, monohydrate and its methyl ester;

4-(3-(4-Acetyl-3-hydroxy-2-propylphenoxy)-2-hydroxypropylthio)-2-fluorobenzeneacetic acid-S-oxide and its methyl ester;

4-(3-(4-Acetyl-3-hydroxy-2-propylphenoxy)-2-hydroxypropylsulfonyl)-2-fluorobenzeneacetic acid; and 4-(3 -(4-Acetyl-3-hydroxy-2-propylphenoxy)- 1 -propenylsulfonyl)-2-fluorobenzeneacetic acid and its methyl ester;

4-(3-(4-Acetyl-3-hydroxy-2-propylphenoxy)propylthio-3-fluorobenzeneacetic acid and its methyl ester;

4-(3-(4-Acetyl-3-hydroxy-2-propylphenoxy)-2-hydroxypropylthio)-3-fluorobenzeneacetic acid and its methyl ester;

4-(3 -(4-Acetyl-3 -hydroxy-2-propylphenoxy)-propylthio-3-chlorobenzeneacetic acid and its methyl ester;

4-(3-(4-Acetyl-3 -hydroxy-2-propylphenoxy)-propylthio) -3 -chlorobenzeneacetic acid-S-oxide and its methyl ester;

4-(3-(4-Acetyl-3-hydroxy-2-propylphenoxy)-propylsulfonyl)-3-chlorobenzeneacetic acid and its methyl ester;

4-(3-(4-Acetyl-3-hydroxy-2-propylphenoxy)-2-hydroxypropylthio)-3-chlorobenzeneacetic acid and its methyl ester;

4-(3-(4-Acetyl-3-hydroxy-2-propylphenoxy)-2-hydroxypropylthio)-3-chlorobenzeneacetic acid-S-oxide and its methyl ester;

4-(3-(4-Acetyl-3-hydroxy-2-propylphenoxy)-2-hydroxypropylsulfonyl)-3-chlorobenzeneacetic acid and its methyl ester;

4-(3 -(4-Acetyl-3-hydroxy-2-propylphenoxy)-propylthio)benzeneacetic acid and its methyl ester;

4-(3-(4-Acetyl-3-hydroxy-2-propylphenoxy)-propylsulfonyl)-benzeneacetic acid and its methyl ester;

4-(3-(4-Acetyl-3-hydroxy-2-propylphenoxy)-2-methylpropylthio)-benzeneacetic acid and its methyl ester;

4-(3-(4-Acetyl-3-hydroxy-2-propylphenoxy)-2-hydroxypropylthio)-benzeneacetic acid and its methyl ester;

4-(3-(4-Acetyl-3-hydroxy-2-propylphenoxy)-2-hydroxypropylthio)-3 -fluorobenzoic acid and its methyl ester;

4-(3-(4-Acetyl-3-hydroxy-2-propylphenoxy)-2-hydroxypropylthio)-3-fluorobenzoic acid and its methyl ester;

4-(3 -(4-Acetyl-3 -hydroxy-2-propylphenoxy)-2-hydroxypropylsulfonyl)-3-fluorobenzoic acid and its methyl ester;

4-(3 -(4-Acetyl-3 -hydroxy-2-propylphenoxy)-propylthio)-3 -fluorobenzoic acid-S-oxide, methyl ester and its methyl ester;

4-(3-(4-Acetyl-3-hydroxy-2-propylphenoxy)-propylsulfonyl)-3-fluorobenzoic acid its methyl ester; and 4-(3-(4-Acetyl-3-hydroxy-2-propylphenoxy)-propylcyanamido)-benzeneacetic acid and its methyl ester.

5. A method for the treatment or prevention of diabetes which comprises administering to a diabetic patient an effective amount of a compound of claim 1 in combination with a sulfonylurea, fibrate, HMG-CoA reductase inhibitor, beta-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue or insulin.

6. A method for treating obesity which comprises administering to a patient in need thereof an effective amount of a compound of formula XI or XII:

and

-continued

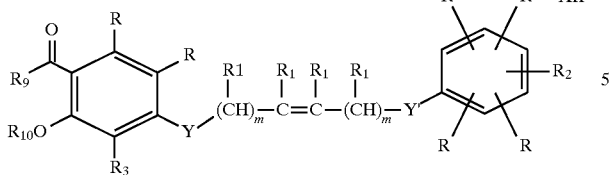

or a pharmaceutically acceptable salt or acid addition salt thereof, wherein:

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

Y' is sulfur, sulfoxide, sulfone;

$R_{11}$ is H, alkyl of 1–4 carbon atoms which may be straight chain or branched; alkanoyl of 1–4 carbon atoms which may be straight chain or branched; phenylsulfonyl; tosyl; $NR_{12}$ wherein $R_{12}$ is H, alkyl of 1–4 carbon atoms which may be straight chain or branched; or

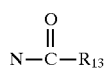

wherein $R_{13}$ is alkyl of 1–4 carbon atoms which may be straight chain or branched, alkoxy of 1–4 carbon atoms which may be straight chain or branched; N—CN, $CH_2$, or C=O;

Y is Y' and oxygen;

each $R_1$ is independently hydrogen or alkyl of 1–3 carbon atoms;

each m is independently an integer from 0–6;

$R_2$ is

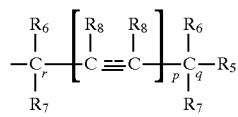

each $R_6$ is independently H or alkyl of 1–4 carbons;
each $R_7$ is independently H, OH, or alkyl of 1–4 carbons;
each $R_8$ is independently H, or alkyl of 1–4 carbons, and is absent when a triple bond is present;

$R_5$ is $COOR_4$; $CH_2OH$; CHO; tetrazole; $NHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is

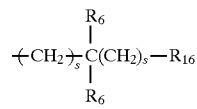

wherein each s is independently 0–3;

$R_{16}$ is

A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

$R_{14}$ is OH, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl, acyl of 1 to 6 carbon atoms or perfluoroalkyl of 1 to 4 carbon atoms;

r an q are each independently 0–20 provided that the total of r and q does not exceed 20;

p is 0 or 1;

$R_3$ is alkyl of 1 to 6 carbon atoms which may be straight chain or branched; or alkenyl of 3 to 6 carbon atoms which may be straight chain or branched as illustrated in formulas IV and V;

$R_9$ is alkyl of 1 to 6 carbon atoms which may be straight chain or branched; alkoxy of 1 to 6 carbon atoms which may be straight chain or branched; or $(CH_2)_rR_5$; and $R_{10}$ is H; alkyl of 1 to 6 carbon atoms which may be straight chain or branched;

or $R_4OCH_2$—.

7. A method according to claim 6 in combination with a fenfluramine, dexfenfluramine, phentiramine or δ3 adrenergic receptor agonist.

8. A method for lowering triglyceride levels which comprises administering to a patient needing lower triglyceride an effective amount of a compound of formula XI or XII:

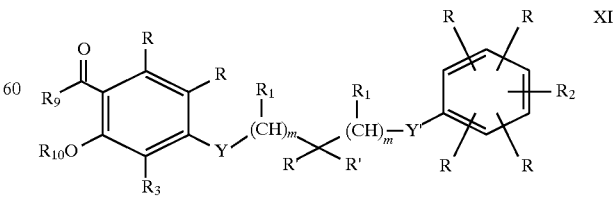

and

-continued

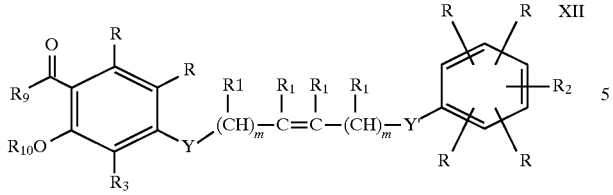

or a pharmaceutically acceptable salt or acid addition salt thereof, wherein:

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

Y' is sulfur, sulfoxide, sulfone;

$R_{11}$ is H, alkyl of 1–4 carbon atoms which may be straight chain or branched; alkanoyl of 1–4 carbon atoms which may be straight chain or branched; phenylsulfonyl; tosyl; $NR_{12}$ wherein $R_{12}$ is H, alkyl of 1–4 carbon atoms which may be straight chain or branched; or

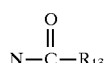

wherein $R_{13}$ is alkyl of 1–4 carbon atoms which may be straight chain or branched, alkoxy of 1–4 carbon atoms which may be straight chain or branched; N—CN, $CH_2$, or C=O;

Y is Y' and oxygen;

each $R_1$ is independently hydrogen or alkyl of 1-3 carbon atoms;

each m is independently an integer from 0–6;

$R_2$ is

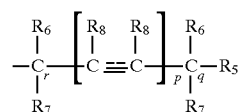

each $R_6$ is independently H or alkyl of 1–4 carbons;
each $R_7$ is independently H, OH, or alkyl of 1–4 carbons;
each $R_8$ is independently H, or alkyl of 1–4 carbons, and is absent when a triple bond is present;

$R_5$ is $COOR_4$; $CH_2OH$; CHO; tetrazole; $NHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is

wherein each s is independently 0–3;

$R_{16}$ is
A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

R14 is OH, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl, acyl of 1 to 6 carbon atoms or perfluoroalkyl of 1 to 4 carbon atoms;

r an q are each independently 0–20 provided that the total of r and q does not exceed 20;

p is 0 or 1;

$R_3$ is alkyl of 1 to 6 carbon atoms which may be straight chain or branched; or alkenyl of 3 to 6 carbon atoms which may be straight chain or branched as illustrated in formulas IV and V;

$R_9$ is alkyl of 1 to 6 carbon atoms which may be straight chain or branched; alkoxy of 1 to 6 carbon atoms which may be straight chain or branched; or $(CH_2)_rR_5$; and $R_{10}$ is H; alkyl of 1 to 6 carbon atoms which may be straight chain or branched;

or $R_4OCH_2$—.

9. A method for halting, preventing or reducing the risk of developing atherosclerosis and related diseae events in a patient in need of such treatment, comprising the administration of a pharmaceutically effective amount of a compound of formula XI or XII:

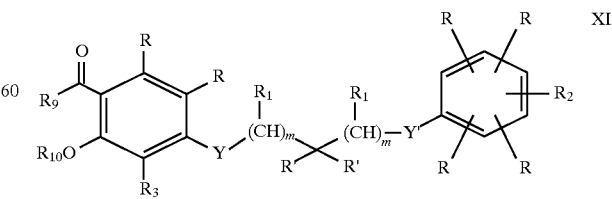

and

-continued

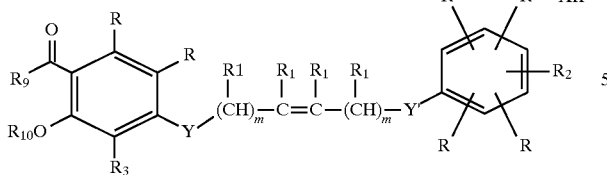

or a pharmaceutically acceptable salt or acid addition salt thereof, wherein:

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

Y' is sulfur, sulfoxide, sulfone;

$R_1$ is H, alkyl of 1–4 carbon atoms which may be straight chain or branched; alkanoyl of 1–4 carbon atoms which may be straight chain or branched; phenylsulfonyl; tosyl; $NR_{12}$ wherein $R_{12}$ is H, alkyl of 1–4 carbon atoms which may be straight chain or branched; or

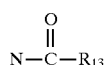

wherein $R_{13}$ is alkyl of 1–4 carbon atoms which may be straight chain or branched, alkoxy of 1–4 carbon atoms which may be straight chain or branched; N—CN, $CH_2$, or C=O;

Y is Y' and oxygen;

each $R_1$ is independently hydrogen or alkyl of 1–3 carbon atoms;

each m is independently an integer from 0–6;

$R_2$ is

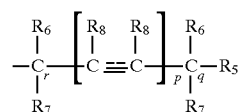

each $R_6$ is independently H or atkyl of 1–4 carbons;
each $R_7$ is independently H, OH, or alkyl of 1–4 carbons;
each $R_8$ is independently H, or alkyl of 1–4 carbons, and is absent when a triple bond is present;

$R_5$ is $COOR_4$; $CH_2OH$; CHO; tetrazole; $NHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is

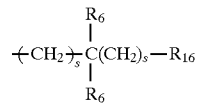

wherein each s is independently 0–3;

$R_{16}$ is
A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

$R_{14}$ is OH, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl, acyl of 1 to 6 carbon atoms or perfluoroalkyl of 1 to 4 carbon atoms;

r an q are each independently 0-20 provided that the total of r and q does not exceed 20;

p is 0 or 1;

$R_3$ is alkyl of 1 to 6 carbon atoms which may be straight chain or branched; or alkenyl of 3 to 6 carbon atoms which may be straight chain or branched as illustrated in formulas IV and V;

$R_9$ is alkyl of 1 to 6 carbon atoms which may be straight chain or branched; alkoxy of 1 to 6 carbon atoms which may be straight chain or branched; or $(CH_2)_rR_5$; and $R_{10}$ is H; alkyl of 1 to 6 carbon atoms which may be straight chain or branched;

or $R_4OCH_2$—.

10. A method according to claim 9 wherein the compound has an $IC_{50}$ equal to or less than 10 μM in the hPPARδ binding assay and an $EC_{50}$ equal to or less than 10 μM in the hPPARδ transactivation assay.

11. The method of claim 10 wherein the compound has an $IC_{50}$ equal to or less than 100 nM in the hPPARδ binding assay and an $EC_{50}$ equal to or less than 100 nM in the hPPARδ transactivation assay.

12. The method of claim 11 wherein the compound has an $IC_{50}$ equal to or less than 50 nM in the hPPARδ binding assay and an $EC_{50}$ equal to or less than 50 nM in the hPPARδ transactivation assay.

13. The method of claim 12 wherein the compound has an $IC_{50}$ equal to or less than 10 nM in the hPPARδ binding assay and an $EC_{50}$ equal to or less than 10 nM in the hPPARδ transactivation assay.

14. A method for raising high densisty lipoprotein plasma levels in a patient in need of such treatment, comprising the administration of a pharmaceutically effective amount of a compound of formula XI or XII:

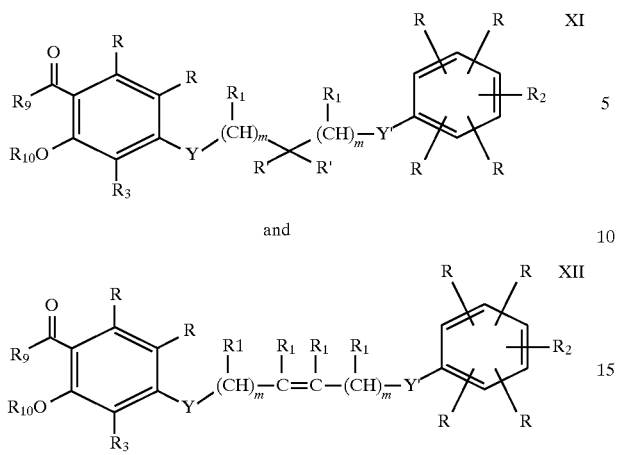

and or a pharmaceutically acceptable salt or acid addition salt thereof, wherein:

each R is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$ wherein $R_4$ is H or alkyl of 1 to 6 carbon atoms which may be straight chain or branched; $COOR_4$; $CH_2OR_4$; formyl; CN; trifluoromethylthio; or nitro;

each R' is independently $R_4$; $OR_4$; $COOR_4$; $N(R_4)_2$; $SR_4$; $CH_2OR_4$; CHO; or together R' and R' are O; $CH_2$; or

Y' is sulfur, sulfoxide, sulfone;

$R_{11}$ is H, alkyl of 1–4 carbon atoms which may be straight chain or branched; alkanoyl of 1–4 carbon atoms which may be straight chain or branched; phenylsulfonyl; tosyl; $NR_{12}$ wherein $R_{12}$ is H, alkyl of 1–4 carbon atoms which may be straight chain or branched; or

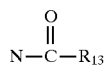

wherein $R_{13}$ is alkyl of 1–4 carbon atoms which may be straight chain or branched, alkoxy of 1–4 carbon atoms which may be straight chain or branched; N—CN, $CH_2$, or C=O;

Y is Y' and oxygen;

each $R_1$ is independently hydrogen or alkyl of 1–3 carbon atoms;

each m is independently an integer from 0–6;

$R_2$ is

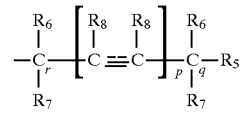

each $R_6$ is independently H or alkyl of 1–4 carbons;
each $R_7$ is independently H, OH, or alkyl of 1–4 carbons;
each $R_8$ is independently H, or alkyl of 1–4 carbons, and is absent when a triple bond is present;
$R_5$ is $COOR_4$; $CH_2OH$; CHO; tetrazole; $NHSO_2R_{14}$; hydroxymethylketone; CN; $CON(R_7)_2$; a monocyclic or bicyclic heterocyclic ring containing an acidic hydroxyl group; or $COOR_{15}$ where $R_{15}$ is

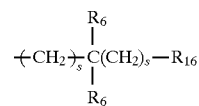

wherein each s is independently 0–3;

$R_{16}$ is
A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
B) the radical W—$R_{17}$ wherein W is O, S or NH and $R_{17}$ contains up to 21 carbon atoms and is (1) a hydrocarbon radical or (2) an acyl radical of an organic acyclic or monocyclic carboxylic acid containing not more than 1 heteroatom in the ring;

R14 is OH, alkyl or alkoxy of 1 to 6 carbon atoms, phenyl or phenyl substituted by alkyl or alkoxy groups of 1 to 3 carbon atoms, halogen, hydroxy, haloalkyl, COOH, CN, formyl, acyl of 1 to 6 carbon atoms or perfluoroalkyl of 1 to 4 carbon atoms;

r an q are each independently 0–20 provided that the total of r and q does not exceed 20;

p is 0 or 1;

$R_3$ is alkyl of 1 to 6 carbon atoms which may be straight chain or branched; or alkenyl of 3 to 6 carbon atoms which may be straight chain or branched as illustrated in formulas IV and V;

$R_9$ is alkyl of 1 to 6 carbon atoms which may be straight chain or branched; alkoxy of 1 to 6 carbon atoms which may be straight chain or branched; or $(CH_2)_rR_5$; and $R_{10}$ is H; alkyl of 1 to 6 carbon atoms which may be straight chain or branched;

or $R_4OCH_2$—.

15. A method according to claim 14 wherein the compound has an $IC_{50}$ equal to or less than 10 μM in the hPPARδ binding assay and an $EC_{50}$ equal to or less than 10 μM in the hPPARδ transactivation assay.

16. The method of claim 15 wherein the compound has an $IC_{50}$ equal to or less than 100 nM in the hPPARδ binding assay and an $EC_{50}$ equal to or less than 100 nM in the hPPARδ transactivation assay.

17. The method of claim 16 wherein the compound has an $IC_{50}$ equal to or less than 50 nM in the hPPARδ binding assay and an $EC_{50}$ equal to or less than 50 nM in the hPPARδ transactivation assay.

18. The method of claim 17 wherein the compound has an $IC_{50}$ equal to or less than 10 nM in the hPPARδ binding assay and an $EC_{50}$ equal to or less than 10 nM in the hPPARδ transactivation assay.

19. A method for halting, preventing or reducing the risk of developing atherosclerosis and related disease events which comprises administering to a patient in need thereof an effective amount of a compound of claim 9 in combination with a sulfonylurea, fibrate, HMG-CoA reductase inhibitor, beta-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue or insulin.

20. A method according to claim 19 wherein the compound has an $IC_{50}$ equal to or less than 10 μM in the hPPARδ binding assay and an $EC_{50}$ equal to or less than 10 μM in the hPPARδ transactivation assay.

21. The method of claim 20 wherein the compound has an $IC_{50}$ equal to or less than 100 nM in the hPPARδ binding assay and an $EC_{50}$ equal to or less than 100 nM in the hPPARδ transactivation assay.

22. The method of claim 21 wherein the compound has an $IC_{50}$ equal to or less than 50 nM in the hPPARδ binding assay and an $EC_{50}$ equal to or less than 50 nM in the hPPARδ transactivation assay.

23. The method of claim 22 wherein the compound has an $IC_{50}$ equal to or less than 10 nM in the hPPARδ binding assay and an $EC_{50}$ equal to or less than 10 nM in the hPPARδ transactivation assay.

* * * * *